(12) United States Patent
Avey et al.

(10) Patent No.: US 8,510,057 B1
(45) Date of Patent: Aug. 13, 2013

(54) SUMMARIZING AN AGGREGATE CONTRIBUTION TO A CHARACTERISTIC FOR AN INDIVIDUAL

(75) Inventors: Linda Avey, Los Gatos, CA (US); Andro Rene Hsu, Berkeley, CA (US); Oleksiy Khomenko, Stanford, CA (US); John Michael Macpherson, Palo Alto, CA (US); Joanna Louise Mountain, Menlo Park, CA (US); Brian Thomas Naughton, Mountain View, CA (US); Serge Saxonov, Seattle, WA (US); Anne Wojcicki, Palo Alto, CA (US); Alexander Wong, Palo Alto, CA (US)

(73) Assignee: 23andMe, Inc., Mountain View, CA (US)

( * ) Notice: Subject to any disclaimer, the term of this patent is extended or adjusted under 35 U.S.C. 154(b) by 692 days.

(21) Appl. No.: 12/151,977

(22) Filed: May 8, 2008

Related U.S. Application Data

(60) Provisional application No. 60/999,175, filed on Oct. 15, 2007.

(51) Int. Cl.
*G06F 7/00* (2006.01)
(52) U.S. Cl.
USPC ................. 702/19; 702/20; 703/11; 707/700; 436/501
(58) Field of Classification Search
None
See application file for complete search history.

(56) References Cited

U.S. PATENT DOCUMENTS

| 7,062,752 B2 | 6/2006 | Simpson et al. |
| 2002/0019746 A1 | 2/2002 | Rienhoff et al. |
| 2002/0128860 A1 | 9/2002 | Leveque et al. |
| 2002/0138572 A1 | 9/2002 | Delany et al. |
| 2005/0027560 A1 | 2/2005 | Cook |
| 2005/0164704 A1 | 7/2005 | Winsor |
| 2007/0061085 A1 | 3/2007 | Fernandez |
| 2008/0082955 A1 | 4/2008 | Andreessen et al. |

OTHER PUBLICATIONS

Morrison et al. Am J Epidemiology 2007, 166:1 28-35, online publication Apr. 2007.*
Cancer Epidemiol Biomarkers Prey 2006;15:158-161. Published online Jan. 24, 2006.*

* cited by examiner

*Primary Examiner* — Mary Zeman
(74) *Attorney, Agent, or Firm* — Van Pelt, Yi & James LLP

(57) ABSTRACT

Summarizing an aggregate contribution to a characteristic for an individual is disclosed, including determining the characteristic to be evaluated, identifying one or more markers associated with the characteristic, retrieving the measurement of the individual for each of the one or more markers from a database of individuals' markers, retrieving a statistical factor that measures the association between the marker associated with the characteristic and the characteristic for each of the one or more markers from the marker database, and determining the aggregate contribution based at least in part on the retrieved statistical factors.

18 Claims, 6 Drawing Sheets

SUMMARIZING AN AGGREGATE CONTRIBUTION TO A CHARACTERISTIC FOR AN INDIVIDUAL

CROSS REFERENCE TO OTHER APPLICATIONS

This application claims priority to U.S. Provisional Patent Application No. 60/999,175 entitled GENE JOURNAL filed Oct. 15, 2007 which is incorporated herein by reference for all purposes.

BACKGROUND OF THE INVENTION

Recently, interest in genetics and genetic testing has risen as increasing amounts of research show how an individual's genetic information can influence aspects of a person's ancestry, appearance, behavior, and physiology. Genetic testing can provide information to help individuals understand areas of potential concern to discuss with their doctors, and together with a doctor, can help individuals make informed decisions about medical management and lifestyle choices. Typical genetic testing solutions allow an individual to order a particular genetic test, such as for type 2 diabetes. The individual typically receives a summary report having a limited set of results with limited interpretative information. Improvements in the interpretation and reporting of genetic test results would be useful.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Figure 1:
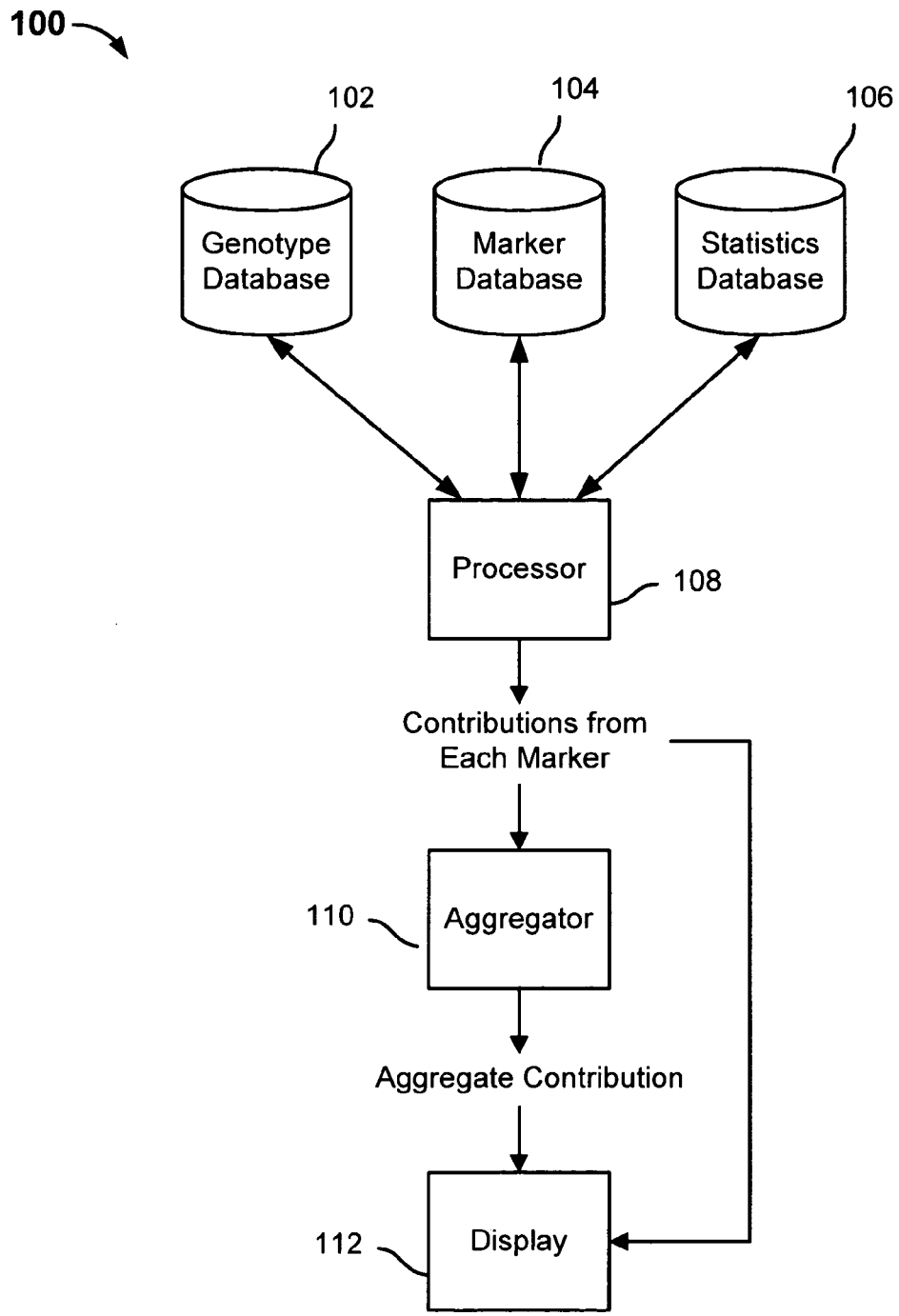
FIG. 1 is a block diagram illustrating an embodiment of a system for determining an aggregate contribution to a characteristic for an individual with a specific marker measurement, for instance, a genotype.

FIG. 1 is a block diagram illustrating an embodiment of a system for determining an aggregate contribution to a characteristic for an individual with a specific marker measurement, for instance, a genotype. The aggregate contribution may also allow an individual to add non-genetic factors to the calculation of the aggregate contribution, including other biomarkers, family history and environmental factors. A characteristic, as used herein, includes a phenotypic characteristic, trait, or condition of an individual. Examples of characteristics include eye color, ability to taste a bitter flavor in raw broccoli, type 2 diabetes, etc. A contribution, as used herein, refers to a measure of the association between a characteristic and an individual based on the individual's marker measurements, including genetics as well as any non-genetic information added by the individual. For example, a contribution may be an odds or probability that an individual has or will develop a characteristic.

In the example shown, processor 108 interacts with genotype database 102, marker database 104, and statistics database 106. Using data obtained from these databases, processor 108 determines contributions associated with each of a set of one or more markers associated with a characteristic. Markers, as used herein, are measurable factors, categorical or quantitative, that are associated with characteristics of individuals. Markers may include genetic markers (e.g., single nucleotide polymorphisms (SNPs)), other biomarkers (e.g., epigenetic markers or cholesterol level), any other appropriate markers (e.g., family history or weight) or combinations of any of the above (e.g. the joint or conditional risk ratio for a SNP and an environmental condition such as smoking status). Contributions from each marker are aggregated at aggregator 110 into an aggregate contribution. The aggregate contribution and/or contributions from each marker are displayed on display 112.

Although SNPs may be described in some of the examples herein, other markers may be used instead of or in addition to SNPs in various embodiments.

Genotype database 102 contains genetic information for a plurality of individuals, where genetic information could include genotyping data, such as SNP data for an individual. Marker database 104 contains information that measures the association between various markers and characteristics. For example, marker database 104 may include an entry that includes:

Ethnicity: European
Ages: 20-39
Characteristic: type 2 diabetes
Marker: TCF7L2
Possible genotypes and odds ratio for each genotype: AA 1.0, AC 1.5, CC 2.0

In this example, the odds ratio indicates the odds that a person having that genotype together with a specified ethnicity and age range will have type 2 diabetes relative to the odds that a person having the AA genotype will have type 2 diabetes (which is why the odds ratio for AA is 1.0). This is the definition used in some association studies. Other traits may incorporate additional modifying non-genetic information, such as other biomarkers, family history, or environmental factors. In other embodiments, other statistical factors besides an odds ratio may be provided (e.g., risk ratio or hazard ratio). In some embodiments, data in marker database 104 is based on genetic studies, such as association studies or linkage studies. These are research studies that produce as output statistical factors (e.g., odds ratios) or deterministic rules that quantify the association between a marker associated with a characteristic and the characteristic. In some embodiments, statistical factors are stored for specified combinations of genotypes from two or more SNPs (e.g., the joint or conditional odds ratios for a pair of SNPs (i.e., an epistatic interaction)).

In some embodiments, entries in marker database 104 are generated by users or third parties. A third party, for example a geneticist, may annotate a putative association between a marker or markers and a characteristic. This annotation may take the form of a mapping from measurements of a marker or a set of markers to textual descriptions of the characteristic in question and/or to statistical factors. All such third party annotations will be noted as such and as not generated by the company.

Statistics database 106 contains information such as incidence or prevalence data for a characteristic (e.g., 10% of people of European ancestry between the ages of 20-39 are diagnosed with type 2 diabetes) and marker frequency data associated with the incidence data (e.g., of the people in the incidence data study, 20% had genotype AA, 60% had genotype AC, and 20% had genotype CC). The marker frequency data may come from the same source as the incidence data, or from a marker frequency database that can be mapped to the same population as the incidence data (e.g., the Hapmap database). We define populations as granularly as the marker association, incidence, and genotype frequency data permit (e.g., European, Asian, and African).

The statistical information from statistics database 106 can be combined with the information in marker database 104 to obtain information that is more relevant to an individual with a particular set of marker measurements, as more fully described below.

In some embodiments, elements 102-110 are associated with a website hosted by a web server that is coupled to a network, such as the Internet. Display 112 is displayed by a web browser running on a client device that is coupled to the network.

Figure 2:
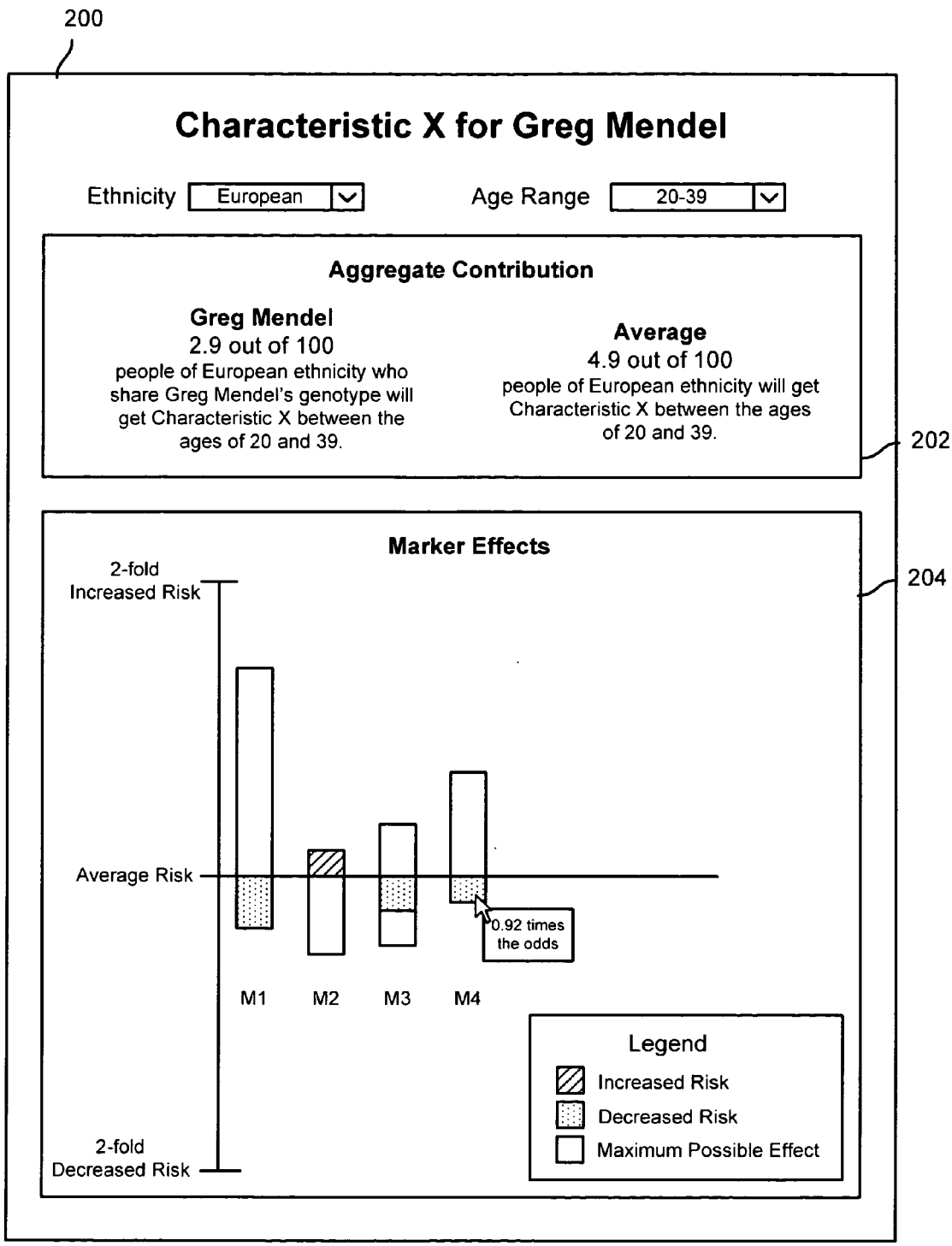
FIG. 2 is a diagram illustrating an embodiment of an interface for displaying contributions to a characteristic for an individual.

FIG. 2 is a diagram illustrating an embodiment of an interface for displaying contributions to a characteristic for an individual. In the example shown, the characteristic is X and the individual is Greg Mendel (not his real name, although a real person available as part of our reference database for viewing). For example, X may be a trait (e.g., eye color) or condition (e.g., type 2 diabetes). In some embodiments, interface 200 is displayed by display 112 of FIG. 1.

Marker effects box 204 shows the approximate effects of Greg Mendel's genotype at four SNPs that are associated with characteristic X. The bar chart represents the change in odds that certain genotypes contribute to the estimated incidence of this characteristic for people with Greg Mendel's measurements at four markers. The horizontal line represents an estimate of the average person's probability of having or developing the characteristic in a particular population subset chosen by the user. Each bar represents the contribution of a single marker to the odds of having or developing the characteristic. In some embodiments, the bars are labeled with a SNP identifier (e.g., rs1234567). In some embodiments, the bars are labeled with the gene the SNP is closest to (e.g., TCF7L2). In some embodiments, the height of each bar is determined by the log of the odds ratio. In some embodiments, a bar may represent a combination of genotypes from SNPs (e.g., joint odds of genotypes from a pair of SNPs) or may represent the contribution of one genotype conditioned on another (e.g., the height of the bar for genotype AA of SNP X may vary depending on the genotype of SNP Y).

Higher, slashed bars indicate increased risk from the average, while lower, dotted bars indicate decreased risk from the average. In this example, an increased risk compared to the average is associated with marker M2 and a decreased risk compared to the average is associated with markers M1, M3, and M4. The white bars show the maximum possible effects for the possible genotypes at the marker or the full range of contributions to risk made by a given SNP. As shown, hovering a cursor over a bar causes a tooltip (small box) to be displayed that indicates the odds for Greg Mendel compared to the average odds for that marker. In this example, the cursor is hovering over the bar for marker M4, and the tooltip indicates that Greg Mendel's odds of having or getting or having characteristic X is 0.92 times the average risk. Examples of how these computations are made are more fully described below.

Aggregate contribution box 202 shows the aggregate contribution of the effects from all the markers (M1-M4 in this example). Incidence is a measure of how often people in a population develop or are diagnosed with a particular condition in a given period of time, and is usually measured in events per person-year. Aggregate contribution box 202 shows an estimate of incidence in two different contexts: average incidence, and a genotype-specific incidence value.

Incidence may also be thought of as an individual's chance of being diagnosed with a condition during a given period of time (assuming that he or she did not have the condition to begin with). A 100% chance is a sure thing. A 0% chance means that the event will never occur. Saying that "25 people out of 100" will be diagnosed with a condition over a given time period is another way to describe a 25% chance of getting it (or odds of 1-to-3 on getting it).

The marker-measurement-specific incidence value (Greg Mendel's incidence value) is an estimate of how many individuals in a population composed of people with a particular set of marker measurements are likely to be diagnosed with a condition over a given age range and with a given ethnicity. In some embodiments, the estimate is based on the current state of biomedical literature and is related only to a particular genotype, age or age range, and ethnicity, but not to the environment. In some embodiments, non-genetic factors, such as other biomarkers, family history, and environmental markers are also accounted for. Examples of computing a genotype-specific incidence value are discussed more fully below.

Interface 200 includes a pull-down menu to select markers, including ethnicity and age range. In this example, if a different ethnicity and/or age range is selected, the aggregate contributions shown in box 202 and the marker effects shown in box 204 will be updated to reflect the new ethnicity and/or age range. The available ethnicities and age ranges depend on the availability of this data from scientific studies. In some embodiments, the ethnicity may be determined based on a user's designated ethnicity or automatically determined based on a user's genetic data. Similarly, the age of the user may be provided by the user. In some cases, the pull-down menu defaults to the designated or automatically determined ethnicity, and an appropriate age range.

Figure 3:
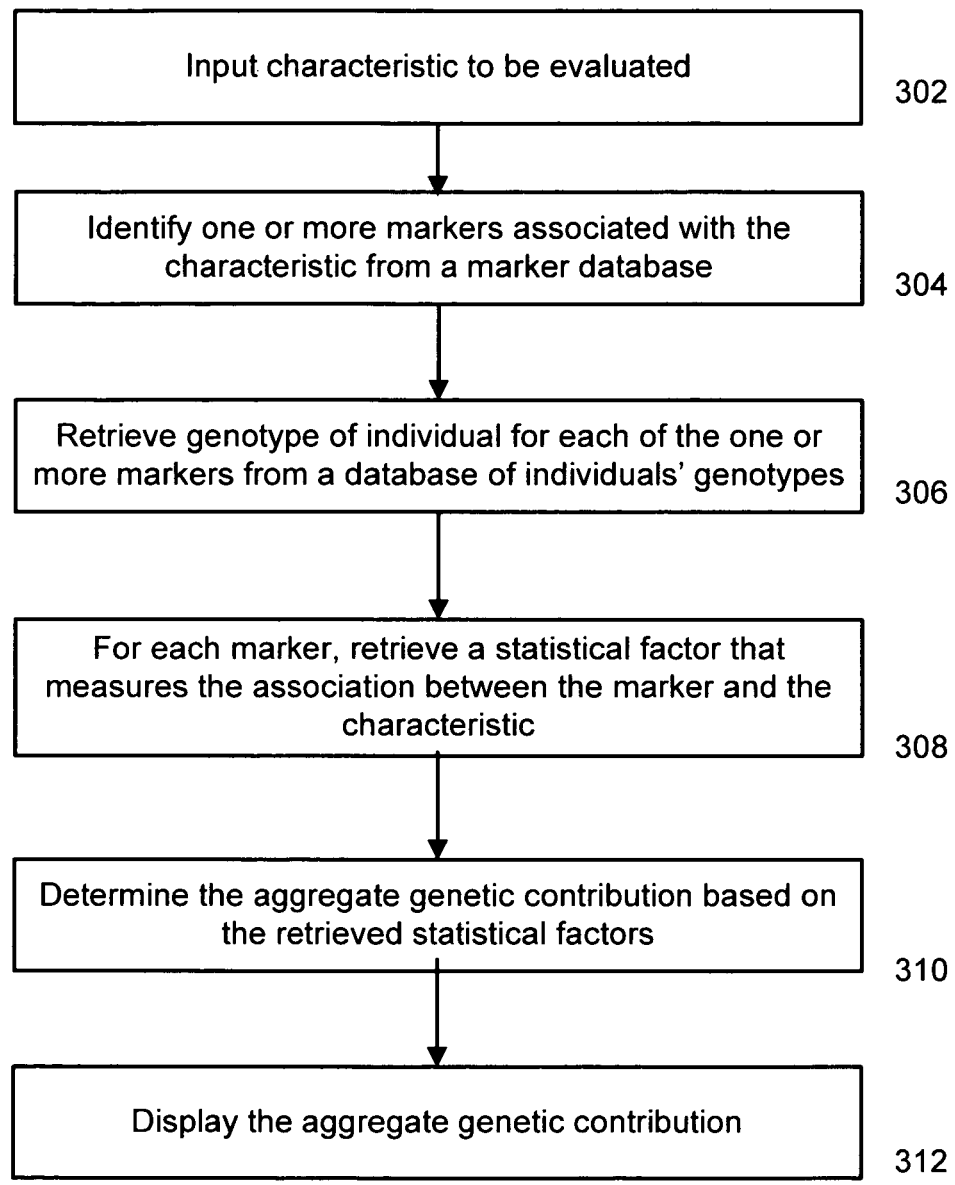
FIG. 3 is a flow chart illustrating an embodiment of a process for summarizing an aggregate contribution to a characteristic for an individual.

FIG. 3 is a flow chart illustrating an embodiment of a process for summarizing an aggregate contribution to a characteristic for an individual. In some embodiments, this process is used to determine an aggregate contribution to characteristic X for Greg Mendel to be displayed in box 202.

At 302, a characteristic to be evaluated is input. For example, to get to interface 200, a user (e.g., Greg Mendel) may choose from a list of available characteristics, such as type 2 diabetes or Crohn's disease.

At 304, one or more markers associated with the characteristic are identified. For example, in FIG. 2, for characteristic X, markers M1, M2, M3, and M4 are identified since they are associated with characteristic X through genetic association studies. In some embodiments, the markers are identified using a marker database, which includes data about which markers are associated with various characteristics.

At 306, the genotype of an individual for each of the one or more SNPs is retrieved from a database of individuals' marker measurements. For example, Greg Mendel's genotype at the relevant SNPs for characteristic X (i.e., M1, M2, M3, and M4) are retrieved from genotype database 102.

At 308, for each marker, a statistical factor that measures the association between the marker and the characteristic is retrieved. For example, the statistical factor that is retrieved from marker database 104 is an odds ratio. In some embodiments, the odds ratio is specific to a selected ethnicity and/or age range of an individual. In some embodiments, the odds ratio is computed relative to the odds of the lowest risk marker. In some embodiments, the odds ratio is a normalized odds ratio computed relative to the average odds. The normalized odds ratio accounts for statistical data about disease incidence and genotype frequency, as more fully described below.

At 310, an aggregate genetic contribution is determined based on the retrieved statistical factors. In some embodiments, the aggregate genetic contribution is determined by multiplying the individual marker genetic contributions (statistical factors) with each other, as more fully described below.

At 312, the aggregate genetic contribution is displayed. For example, in FIG. 2, box 202 displays the aggregate genetic contribution. In some embodiments, the individual marker contribution is displayed, as shown in box 204 of FIG. 2.

In some embodiments, steps 304-308 are performed by processor 108, step 310 is performed by aggregator 110, and step 312 is performed by display 112.

Figure 4:
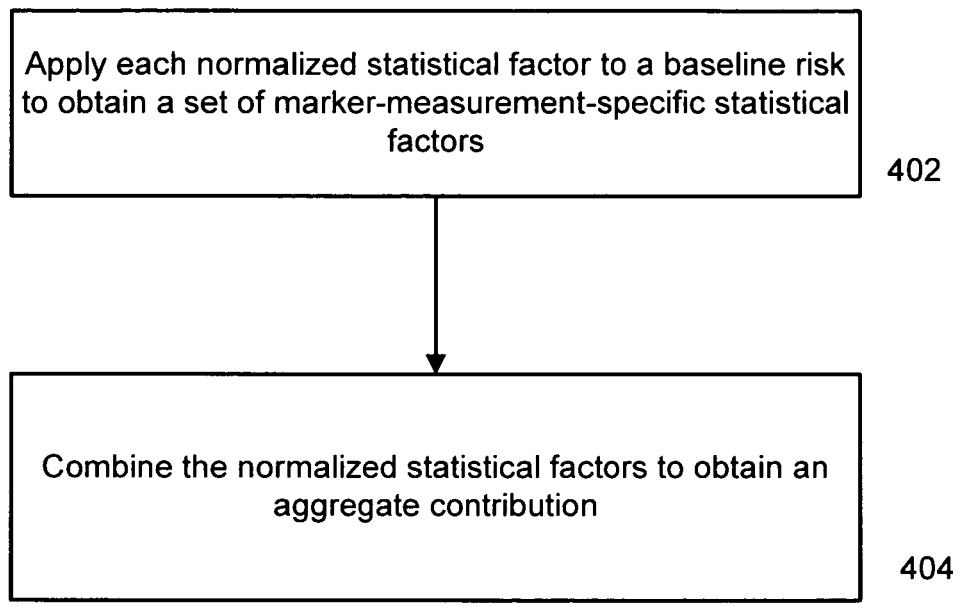
FIG. 4 is a flow chart illustrating an embodiment of a process for determining an aggregate genetic contribution.

FIG. 4 is a flow chart illustrating an embodiment of a process for determining an aggregate genetic contribution. In some embodiments, this process is used to perform step 310 of FIG. 3. At 402, each normalized statistical factor is applied to a baseline risk to obtain a set of marker-measurement-specific statistical factors. In some embodiments, as previously described, the statistical factor is an odds ratio. In some embodiments, baseline risk is average risk. As used herein, risk can include incidence, prevalence, or any other measure of risk. Prevalence is defined as the total number of cases of a characteristic in the population at a given time, or the total number of cases in the population, divided by the number of individuals in the population.

In some embodiments, each normalized statistical factor is a marker-specific contribution. Examples of marker-specific contributions are shown in box 204 of FIG. 2. For example, the marker-specific contribution for marker M4 is 0.92 times the average odds; that is, the odds of someone with Greg Mendel's genotype of getting or having characteristic X is 0.92 times the average.

Figure 5:
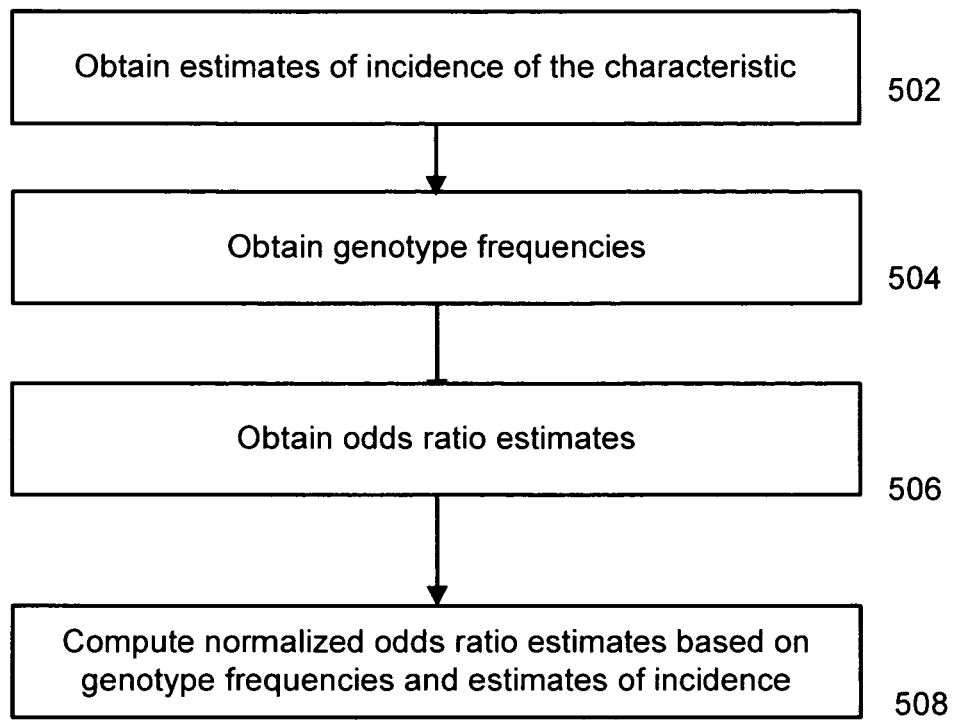
FIG. 5 is a flow chart illustrating an embodiment of a process for obtaining a normalized statistical factor.

In some embodiments, a marker-specific contribution is a genotype-specific risk, i.e., the probability that an individual with that genotype is affected given their genotype, $Pr(D|G_m)$, computed according to FIG. 5.

FIG. 5 is a flow chart illustrating an embodiment of a process for obtaining a normalized statistical factor. In some embodiments, this process is used to perform step 402 of FIG. 4.

In this example, assume a binary characteristic D and a single associated SNP at which there are three possible genotypes $G_1$, $G_2$, and $G_3$, which have odds ratios $OR_1$, $OR_2$, and $OR_3$, respectively. $G_1$ is the genotype with the lowest odds ratio, $OR_1$, and $G_3$ is the genotype with the highest odds ratio, $OR_3$. For example, $G_1$, $G_2$, and $G_3$ could be AA, AC, and CC and $OR_1$, $OR_2$, and $OR_3$ could be 1.0, 1.5, and 2.0. A binary characteristic is a characteristic that has one of two possible values. The individual for whom to estimate the incidence has genotype $G_m : m \in \{1, 2, 3\}$. The quantity to compute is $Pr(D|G_m)$, or the probability that the individual is affected given their genotype. Although a binary characteristic and three genotypes are shown in this example, in other embodiments, any other type of characteristic and number of genotypes may be used.

At 502, estimates of incidence of the characteristic are obtained. For example, the unconditional risk for the characteristic, denoted $Pr(D)$, is obtained for a subpopulation of which the individual is a member. For instance, this may be an estimate of the incidence of type 2 diabetes for Asian subjects between the ages of 20 and 40. This can be obtained from public data sources, such as data collected on incidence and/or prevalence from Centers for Disease Control (CDC) data, or published epidemiological data, for example from disease consortia. At 504, genotype frequencies are obtained. The genotype frequency is the percentage of the studied population having each possible genotype ($G_1$, $G_2$, and $G_3$). For example, estimates of the three genotype frequencies $Pr(G_i)$ are obtained for the same subpopulation. This information can be obtained from databases that store genotype frequencies for different ethnicities, such as dbSNP or SNP500Cancer. At 506, odds ratio estimates are obtained. In some embodiments, the odds ratio estimates are obtained from marker database 104. Odds ratio estimates in marker database 104 may be based on association studies or may be user generated, as previously described. For example, estimates of the three genotype-specific odds ratios $OR_1$, $OR_2$, and $OR_3$ are obtained, where $OR_1$, $OR_2$, and $OR_3$ are odds ratios relative to the lowest odds ratio ($OR_1$), so that $OR_1=1$. In some embodiments, these odds ratios are the statistical factors referred to at 402.

At 508, normalized odds ratio estimates are computed based on genotype frequencies and estimates of incidence. In some embodiments, this is performed as follows. $Pr(D|G_i)$ is computed by solving the following system of equations:

$$Pr(D)=Pr(D|G_1)Pr(G_1)+Pr(D|G_2)Pr(G_2)+Pr(D|G_3)Pr(G_3) \quad (1)$$

$$OR_2 = \frac{Pr(D|G_2)/(1-Pr(D|G_2))}{Pr(D|G_1)/(1-Pr(D|G_1))} \quad (2)$$

$$OR_3 = \frac{Pr(D|G_3)/(1-Pr(D|G_3))}{Pr(D|G_1)/(1-Pr(D|G_1))} \quad (3)$$

Equation 1 follows from basic probability theory, and Equations 2 and 3 follow from the definition of an odds ratio. The estimated genotype-specific risk at the single locus is then $Pr(D|G_m)$.

From equations 1, 2, and 3, $OR_2$, $OR_3$, $Pr(D)$, $Pr(G_1)$, $Pr(G_2)$, and $Pr(G_3)$ are known. The quantities of interest, $Pr(D|G_1)$, $Pr(D|G_2)$, and $Pr(D|G_3)$ are unknown. $Pr(D|G_m)$ can be calculated in a number of ways, including with a numerical root solver, such as Newton-Raphson.

To obtain the genotype-specific risk relative to the average risk in the population (or normalized odds ratio), compute the quantity $OR_m^* = \text{odds}(D|G_m)/\text{odds}(D)$, where, for brevity, we have introduced the function $\text{odds}(X) = Pr(X)/(1-Pr(X))$. The inverse odds function will be used later on, and is $\text{odds}^{-1}(X) = Pr(X)/(1+Pr(X))$. The superscript asterisk on $OR_m^*$ is used to distinguish an odds ratio computed relative to the average odds, rather than relative to the lowest odds ratio, which is the definition used in some association studies.

Returning to FIG. 4, at 404, the normalized statistical factors are combined to obtain an aggregate contribution. In some embodiments, an aggregate contribution is a probability $Pr(D|\cap_{k=1}^{K} G_{m_k,k})$ computed as follows.

Assume that the composite odds ratio, $OR_C$, is given by the product of the individual's odds ratios at each locus. Assume that there are K loci of interest, and denote the kth odds ratio of the ith genotype $OR_{i,k}$. Similarly, the normalized odds ratios are denoted $OR_{i,k}^*$. Denote the genotypes at the kth locus $G_{1,k}, G_{2,k}, G_{3,k}$, and denote the individual's genotype at the kth locus $G_{m_k,k}^*$. Thus $$OR_C^* = \prod_{k=1}^{K} OR_{m_k,k}^* \quad (4)$$

The quantity $OR_C^*$ has the interpretation $$OR_C^* = \text{odds}(D|\cap_{k=1}^{K} G_{m_k,k})/\text{odds}(D), \quad (5)$$

where $\text{odds}(D|\cap_{k=1}^{K} G_{m_k,k})$ is the odds for the individual's multilocus genotype. In computing the product, we implicitly assume that the point where $\log(\text{odds}(D))$ intersects the respective logistic regression line for each locus is the same point in each of the individual regression calculations, as would be true if a multiple logistic regression had been performed. Then $$Pr(D|\cap_{k=1}^{K} G_{m_k,k}) = \text{odds}^{-1}[OR_C^* \cdot \text{odds}(D)]. \quad (6)$$

An example of an aggregate contribution $Pr(D|\cap_{k=1}^{K} G_{m_k,k})$ is shown in box 202 of FIG. 2. For example, Greg Mendel has a 2.9 in 100 probability of getting characteristic X given his genotype for markers M1-M4.

Figure 6:
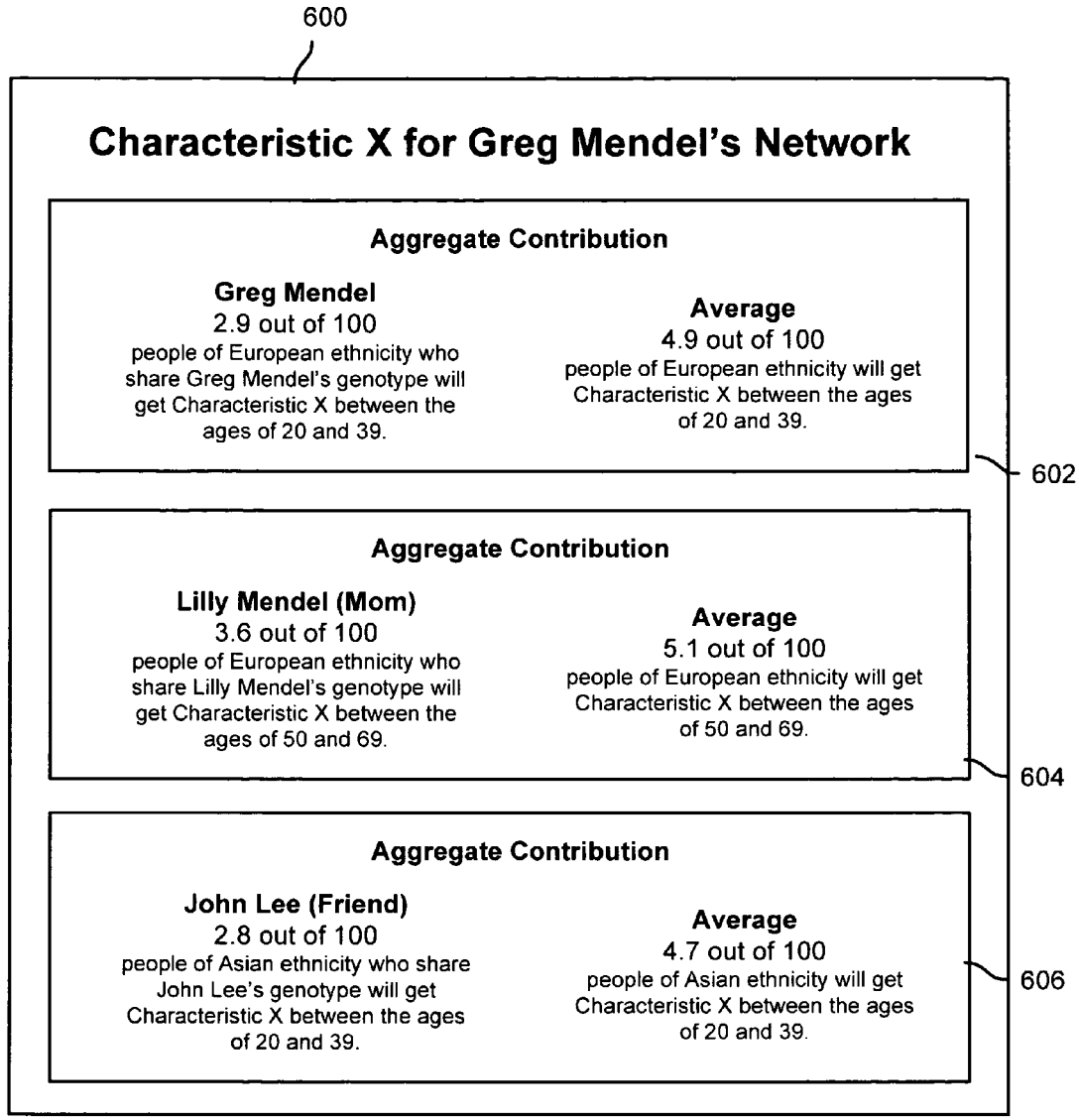
FIG. 6 is a diagram illustrating an embodiment of an interface for displaying contributions to a characteristic for multiple individuals.

FIG. 6 is a diagram illustrating an embodiment of an interface for displaying contributions to a characteristic for multiple individuals. In some embodiments, interface 200 is displayed by display 112 of FIG. 1. In the example shown, the characteristic is X and the individuals are Greg Mendel (the user) and other individuals who have given permission to allow Greg Mendel to view their aggregate contributions to characteristic X. For example, Greg Mendel may have family and/or friends who have enabled sharing of their aggregate contributions to characteristic X with Greg. In this example, Lilly Mendel (his mother), and John Lee (a friend), have enabled sharing with Greg Mendel.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method for summarizing an aggregate contribution to a characteristic for an individual, comprising:
   receiving at a processor, an indication of the characteristic to be evaluated and an indication of an individual to determine the aggregate contribution for, wherein the characteristic is phenotypic;
   identifying, using a processor, a plurality of markers associated with the characteristic;
   retrieving the measurement of the individual for each of the plurality of markers from a database of individuals' markers;
   retrieving a plurality of statistical factors that measure an association between the plurality of markers and the characteristics, including a joint or conditional association between a set of one or more of the plurality of markers and the characteristic; and
   determining the aggregate contribution to the characteristic of the individual based at least in part on the retrieved statistical factors; wherein the aggregate contribution is a probability or an odds ratio;
   outputting display characteristics to be displayed of the aggregate contribution to the characteristic of the individual.

2. A method as recited in claim 1, wherein at least one marker is a genetic marker.

3. A method as recited in claim 1, wherein at least one marker is a single nucleotide polymorphism (SNP).

4. A method as recited in claim 1, wherein the statistical factor is an odds ratio.

5. A method as recited in claim 1, wherein the statistical factor is a normalized odds ratio.

6. A method as recited in claim 1, wherein determining includes taking a product of odds ratios associated with each marker.

7. A method as recited in claim 1, further including providing average odds.

8. A method as recited in claim 1, wherein the statistical factor is based on ancestral group or ethnicity.

9. A method as recited in claim 1, wherein the statistical factor is based on age group.

10. A method as recited in claim 1, wherein determining includes applying each statistical factor to a baseline incidence or prevalence.

11. A method as recited in claim 1, wherein determining includes combining the retrieved statistical factors for the markers.

12. A method as recited in claim 1, wherein determining includes applying each statistical factor to a baseline incidence or prevalence to obtain a set of normalized statistical factors and combining the normalized statistical factors to obtain the aggregate contribution.

13. A method as recited in claim 1, wherein at least one marker is a biomarker.

14. A method as recited in claim 1, wherein at least two statistical factors are associated with different research studies.

15. A method as recited in claim 1, wherein the marker database includes user generated data.

16. A method as recited in claim 1, further including displaying the aggregate contribution of a plurality of individuals.

17. A system for summarizing an aggregate contribution to a characteristic for an individual, comprising:
 a processor configured to:
  receive an indication of the characteristic to be evaluated and an indication of an individual to determine the aggregate contribution for, wherein the characteristic is phenotypic;
  identify a plurality of markers associated with the characteristic;
  retrieve the measurement of the individual for each of the plurality of markers from a database of individuals' markers;
  retrieve a plurality of statistical factors that measure an association between the plurality of markers and the characteristics, including a joint or conditional association between a set of one or more of the plurality of markers and the characteristic; and
  determine the aggregate contribution to the characteristic of the individual based at least in part on the retrieved statistical factors; wherein the aggregate contribution is a probability or an odds ratio;
  output display characteristics to be displayed of the aggregate contribution to the characteristic of the individual; and
 a memory coupled to the processor and configured to provide the processor with instructions.

18. A computer program product for summarizing an aggregate contribution to a characteristic for an individual, the computer program product being embodied in a non-transitory computer readable medium and comprising computer instructions for:
 receiving an indication of the characteristic to be evaluated and an indication of an individual to determine the aggregate contribution for, wherein the characteristic is phenotypic;
 identifying one or more markers associated with the characteristic; identifying using a processor a plurality of markers associated with the characteristic;
 retrieving the measurement of the individual for each of the plurality of markers from a database of individuals' markers;
 retrieving a plurality of statistical factors that measure an association between the plurality of markers and the characteristics, including a joint or conditional association between a set of one or more of the plurality of markers and the characteristic; and
 determining the aggregate contribution to the characteristic of the individual based at least in part on the retrieved statistical factors, wherein the aggregate contribution is a probability or an odds ratio;
 outputting display characteristics to be displayed of the aggregate contribution to the characteristic of the individual.

* * * * *